(12) United States Patent
Carley et al.

(10) Patent No.: US 9,461,393 B2
(45) Date of Patent: Oct. 4, 2016

(54) PHYSICAL SHIELDING FOR ECG ELECTRICAL CONNECTIONS

(71) Applicant: Covidien LP, Mansfield, MA (US)

(72) Inventors: Cynthia Carley, Brimmfield, MA (US); Wayne Biermann, St. Charles, MO (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 14/693,926

(22) Filed: Apr. 23, 2015

(65) Prior Publication Data

US 2015/0311621 A1    Oct. 29, 2015

Related U.S. Application Data

(60) Provisional application No. 61/984,241, filed on Apr. 25, 2014.

(51) Int. Cl.
*H01R 13/46* (2006.01)
*A61B 5/0428* (2006.01)
*H01R 13/52* (2006.01)
(Continued)

(52) U.S. Cl.
CPC .......... *H01R 13/46* (2013.01); *A61B 5/0402* (2013.01); *A61B 5/04286* (2013.01); *H01R 13/5213* (2013.01); *H01R 31/06* (2013.01); *A61B 2562/18* (2013.01); *A61B 2562/221* (2013.01);
(Continued)

(58) Field of Classification Search
CPC .. H01R 13/46; H01R 31/06; H01R 13/5213; H01R 13/6392; H01R 24/54; H01R 13/5224; H01R 13/5216; A61B 5/0402; A61B 5/04286; A61B 2562/221; A61B 2562/18

USPC ................ 439/628, 909, 367, 369, 638, 651
See application file for complete search history.

(56) References Cited

U.S. PATENT DOCUMENTS 1,921,447 A    8/1933  Barnett
2,037,630 A    4/1936  Hudson
(Continued)

FOREIGN PATENT DOCUMENTS

EP          2 412 307 A1    2/2012
WO     WO 2010/129026      11/2010

OTHER PUBLICATIONS

European Extended Search Report dated Sep. 8, 2015 for European Patent Application No. 15164582.7; 6 Pages.

*Primary Examiner* — Neil Abrams
*Assistant Examiner* — Travis Chambers

(57) ABSTRACT

In one aspect, a physical shielding system includes one or more shield components to protect a first ECG electrical connection and a second ECG electrical connection from objects. The first ECG electrical connection is formed between a connector of an ECG lead set and an adapter and the second ECG electrical connection is formed between the adapter and an ECG monitor. In another aspect, an ECG adapter system includes an ECG adapter. The ECG adapter includes a first interface configured to directly couple with a connector of an ECG lead set to form a first ECG electrical connection, a second interface configured to directly couple with an ECG monitor to form a second ECG electrical connection and a shield disposed around the adapter that includes a first opening configured to allow the connector to couple with the adapter and to shield the first ECG electrical connection from objects and a second opening configured to allow the ECG monitor to couple with the adapter and to shield the second ECG electrical connection from objects.

6 Claims, 5 Drawing Sheets

(51) Int. Cl.
*H01R 31/06* (2006.01)
*A61B 5/0402* (2006.01)

(52) U.S. Cl.
CPC ....... *H01R 13/5216* (2013.01); *H01R 13/5224* (2013.01)

(56) References Cited

U.S. PATENT DOCUMENTS

| | | | |
|---|---|---|---|
| 2,127,544 A | | 8/1938 | Holtz |
| 2,458,153 A | * | 1/1949 | Festge ............... H01R 13/4538 439/140 |
| 3,020,516 A | | 2/1962 | Despard |
| 3,059,209 A | | 10/1962 | Bird |
| 3,258,732 A | * | 6/1966 | Martin ................. H01J 29/925 439/269.1 |
| 3,323,096 A | * | 5/1967 | Appleton ............ H01R 13/621 439/320 |
| 3,449,706 A | * | 6/1969 | Carissimi .......... H01R 13/5227 174/67 |
| 3,571,782 A | | 3/1971 | Colbert |
| 3,683,315 A | * | 8/1972 | William ........................ 439/141 |
| 3,740,694 A | * | 6/1973 | Fisher ................. H01R 13/453 439/138 |
| 4,391,481 A | * | 7/1983 | Golden ................. H01R 13/44 439/141 |
| 4,523,296 A | * | 6/1985 | Healy, Jr. ............. G06F 3/0601 439/651 |
| 4,576,428 A | | 3/1986 | DeLuca et al. |
| 4,632,121 A | * | 12/1986 | Johnson ............ A61B 5/04286 439/346 |
| 4,731,032 A | | 3/1988 | Noorily |
| 4,810,199 A | * | 3/1989 | Kar ........................ H01R 13/44 439/141 |
| 4,917,625 A | * | 4/1990 | Haile ................. H01R 13/6392 439/271 |
| 4,944,685 A | * | 7/1990 | Schulte ................. H01R 13/44 439/135 |
| 5,041,000 A | * | 8/1991 | Shotey ............... H01R 13/5213 439/147 |
| 5,080,598 A | * | 1/1992 | Shotey ............... H01R 13/5213 174/67 |
| 5,147,216 A | | 9/1992 | Shotey |
| 5,341,812 A | * | 8/1994 | Allaire ............... A61B 5/04286 600/508 |
| 5,397,243 A | * | 3/1995 | MacMurdo, Sr. ..... H02G 11/00 174/135 |
| 5,401,184 A | | 3/1995 | Sundstrom et al. |
| 5,582,180 A | | 12/1996 | Manset et al. |
| 5,616,046 A | * | 4/1997 | Sundstrom ......... H01R 13/5213 439/367 |
| 5,632,643 A | | 5/1997 | Shepherd et al. |
| 5,762,515 A | * | 6/1998 | Mele ................. H01R 13/6392 439/367 |
| 5,890,930 A | * | 4/1999 | Gerow ................. H01R 31/06 439/651 |
| 6,007,378 A | | 12/1999 | Oeth |
| 6,099,354 A | * | 8/2000 | Troyan ................. H01R 12/721 439/638 |
| 6,250,946 B1 | | 6/2001 | Tardy |
| 6,324,416 B1 | * | 11/2001 | Seibert ................ A61B 5/0416 128/897 |
| 6,350,160 B1 | * | 2/2002 | Feuersanger ...... H01R 13/6456 439/680 |
| 6,526,310 B1 | | 2/2003 | Carter et al. |
| 6,647,286 B1 | | 11/2003 | Kato et al. |
| 6,716,165 B1 | * | 4/2004 | Flanders .............. A61B 5/0006 128/903 |
| 6,945,822 B2 | * | 9/2005 | Flemming .............. H01R 31/06 439/638 |
| 7,011,535 B2 | | 3/2006 | Dickie |
| 7,056,145 B2 | | 6/2006 | Campbell, III et al. |
| 7,090,516 B2 | | 8/2006 | Khemakhem |
| 7,094,080 B2 | * | 8/2006 | Dickie ............... H01R 13/4538 439/141 |
| 7,359,751 B1 | * | 4/2008 | Erickson ............ A61N 1/37241 607/27 |
| 7,513,038 B2 | * | 4/2009 | Koh ................. H01R 13/6205 29/825 |
| 7,618,269 B2 | | 11/2009 | Naro et al. |
| 7,674,121 B2 | | 3/2010 | Khemakhem |
| 7,677,929 B2 | * | 3/2010 | Bradford-Stagg ... H01R 13/639 439/562 |
| 7,707,719 B2 | | 5/2010 | Meister et al. |
| 7,845,966 B2 | * | 12/2010 | Rioufreyt ........... H01R 13/5213 439/137 |
| 7,942,694 B2 | | 5/2011 | Amidon |
| 7,993,167 B2 | | 8/2011 | Keightley et al. |
| 8,062,045 B2 | | 11/2011 | Montena |
| 8,480,428 B1 | * | 7/2013 | Sper ................... H01R 13/5213 439/521 |
| 8,529,288 B2 | * | 9/2013 | Montena ............ H01R 13/5213 439/523 |
| 9,072,444 B2 | * | 7/2015 | Burnes ............. A61B 5/04286 |
| 2002/0165458 A1 | | 11/2002 | Carter et al. |
| 2004/0175983 A1 | | 9/2004 | Davis |
| 2005/0019725 A1 | | 1/2005 | Pagac |
| 2005/0020111 A1 | | 1/2005 | Pagac |
| 2005/0106909 A1 | | 5/2005 | Dickie |
| 2005/0165465 A1 | | 7/2005 | Pianca et al. |
| 2006/0014411 A1 | * | 1/2006 | Stair ................. H01R 13/6392 439/271 |
| 2006/0035508 A1 | * | 2/2006 | Stekelenburg ..... H01R 13/6392 439/369 |
| 2006/0148287 A1 | | 7/2006 | Zahnen et al. |
| 2006/0178047 A1 | * | 8/2006 | Croan ................ H01R 13/6272 439/578 |
| 2009/0124112 A1 | * | 5/2009 | Sokol ..................... H01R 4/70 439/367 |
| 2010/0168547 A1 | | 7/2010 | Kendricks |
| 2011/0004090 A1 | | 1/2011 | Keightley et al. |
| 2011/0092833 A1 | | 4/2011 | Farrior |
| 2012/0028504 A1 | * | 2/2012 | Coggins ............ A61B 5/04286 439/628 |
| 2012/0040557 A1 | * | 2/2012 | Marsh ................. H01R 9/0503 439/585 |
| 2012/0158075 A1 | | 6/2012 | Kaib et al. |
| 2012/0184120 A1 | | 7/2012 | Basta et al. |
| 2013/0345535 A1 | | 12/2013 | Elschenbroich |
| 2014/0084678 A1 | * | 3/2014 | Isaac ..................... H01R 31/06 307/10.1 |
| 2016/0064995 A1 | * | 3/2016 | Schwalbach ........... A47F 7/022 320/108 |

\* cited by examiner

PHYSICAL SHIELDING FOR ECG ELECTRICAL CONNECTIONS

CROSS REFERENCE TO RELATED APPLICATION

This application claims priority from U.S. Provisional Patent Application Ser. No. 61/984,241, filed on Apr. 25, 2014, and entitled "PHYSICAL SHIELDING FOR ECG ELECTRICAL CONNECTIONS," which is incorporated herein by reference in its entirety.

BACKGROUND

Electrocardiograph (ECG) lead systems are widely used to obtain biopotential signals containing information indicative of the electrical activity associated with the heart and pulmonary system. To obtain biopotential signals ECG electrodes are applied to the skin of a patient in various locations and coupled to an ECG device, e.g., an "ECG monitor" or "ECG telemetry." Placement of the electrodes is dependent on the information sought by the clinician.

SUMMARY

In one aspect, a physical shielding system includes one or more shield components to protect a first ECG electrical connection and a second ECG electrical connection from objects. The first ECG electrical connection is formed between a connector of an ECG lead set and an adapter and the second ECG electrical connection is formed between the adapter and an ECG monitor.

The previous aspect may include one or more of the following features. The one or more shield components may include a shield around the adapter. The one or more shield components may include a first shield disposed around the connector of the ECG lead set and a second shield disposed around the adapter.

In another aspect, an ECG adapter system includes an ECG adapter. The ECG adapter includes a first interface configured to directly couple with a connector of an ECG lead set to form a first ECG electrical connection, a second interface configured to directly couple with an ECG monitor to form a second ECG electrical connection and a shield disposed around the adapter that includes a first opening configured to allow the connector to couple with the adapter and to shield the first ECG electrical connection from objects and a second opening configured to allow the ECG monitor to couple with the adapter and to shield the second ECG electrical connection from objects.

DETAILED DESCRIPTION

Figure 1:
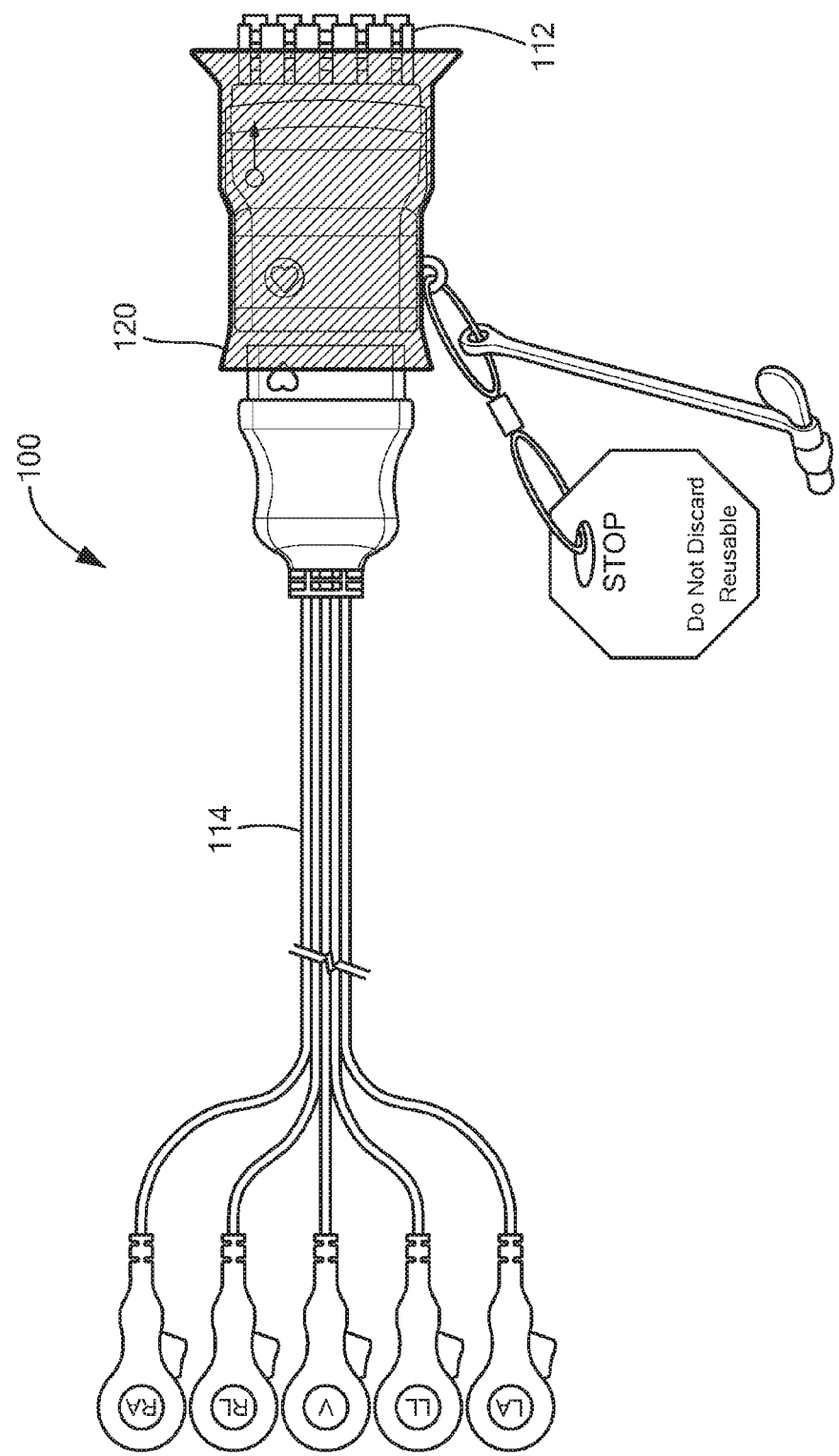
FIG. 1 is a diagram of an example of an electrocardiogram (ECG) lead set configuration with a shield component.
Figure 2:
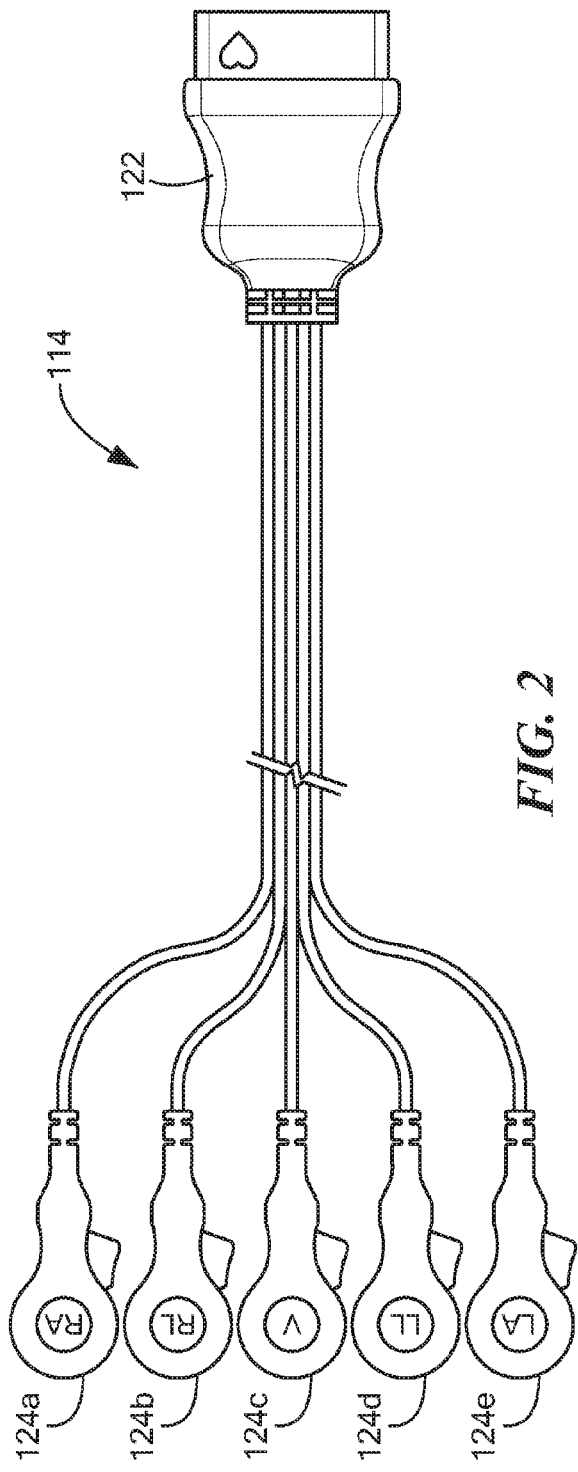
FIG. 2 is a diagram of an ECG lead set in the configuration of FIG. 1.
Figure 3:
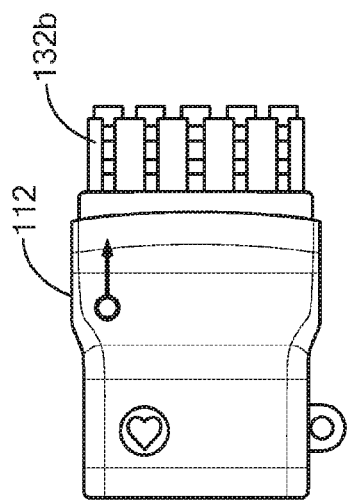
FIG. 3 is a diagram of an adapter in the configuration of FIG. 1.
Figure 4:
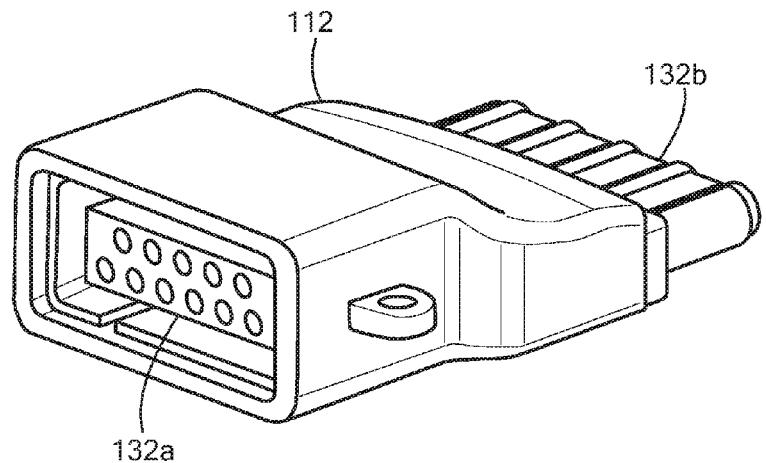
FIG. 4 is an angled view of the adapter.
Figure 5:
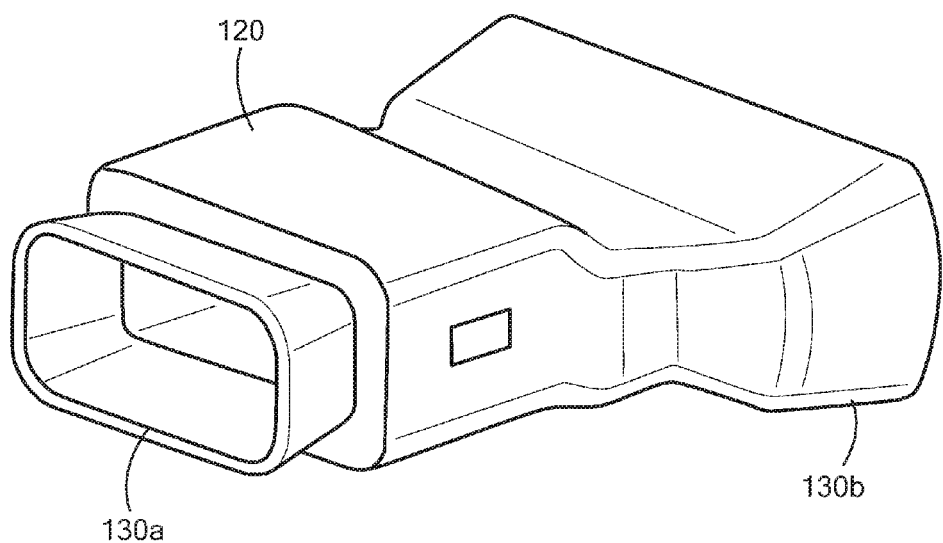
FIG. 5 is an angled view of the shield component of FIG. 1.

Described herein are techniques to protect electrical connections from dirt, debris, fluids and so forth. In one example, the electrical connections are electrical connections used in electrocardiogram (ECG) monitoring. For example, by shielding electrical connections from water, patients may be able to shower or have locations on the patient's body sprayed with water without interfering with ECG monitoring.

Referring to FIGS. 1 to 5, an ECG lead set configuration 100 includes an ECG lead set 114, an adapter 112, and a shield 120. The ECG lead set 114 includes leads 124a-124e and an ECG lead set connector 122. The adapter 112 includes a first interface 132a for coupling with the ECG lead set connector 122 and a second interface 132b for coupling with an ECG monitor (not shown) such as an ECG floor monitor or an ECG telemetry monitor. A first electrical connection is formed between the ECG lead set connector 122 and the first interface 132a of the adapter 112. A second electrical connection is formed between the second interface 132b of the adapter 112 and the ECG monitor. In one example, the connector includes 10 pins and the interface 132a is a socket to receive the 10 pins form the connector 122.

The shield 120 includes a funnel 130a at one end and a funnel 130b at the other end. The shield 120 is made of flexible material such as silicone, for example, and has a snug fit with the adapter 120. For example, the shield 120 which is shaped similar to the adapter 112 is slid on to the adapter 112. The funnel 130a is configured to allow the ECG lead set connector 122 to pass through to connect with the first interface 132a. The funnel 130b is configured to allow a connector (not shown) from the ECG monitor to pass through to connect with the second interface 132a. With this arrangement the first and second electrical connections are shielded, for example, from physical objects such as dirt, debris, fluids and so forth.

Figure 6:
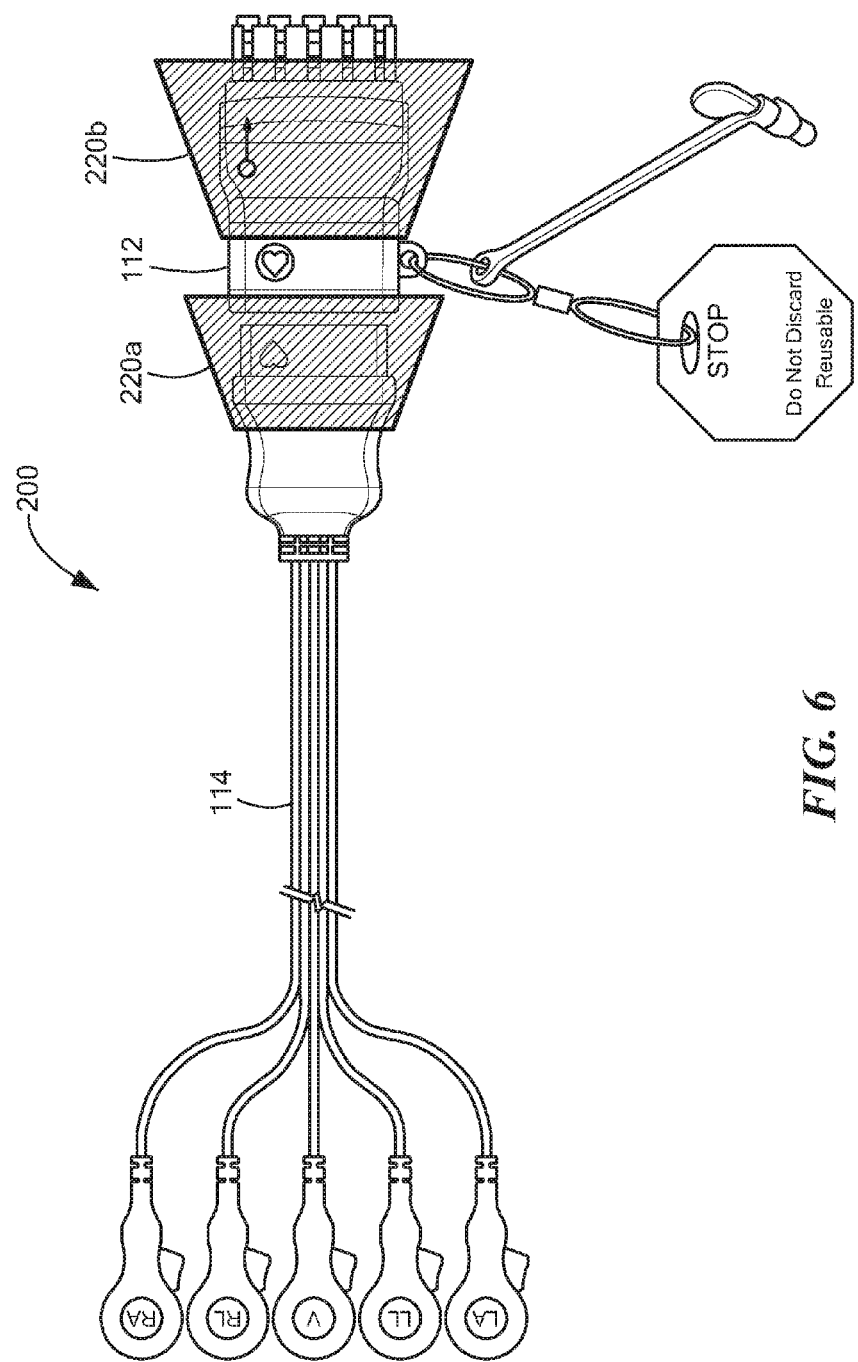
FIG. 6 is a diagram of another example of the ECG lead set configuration with two shield components.
Figure 7:
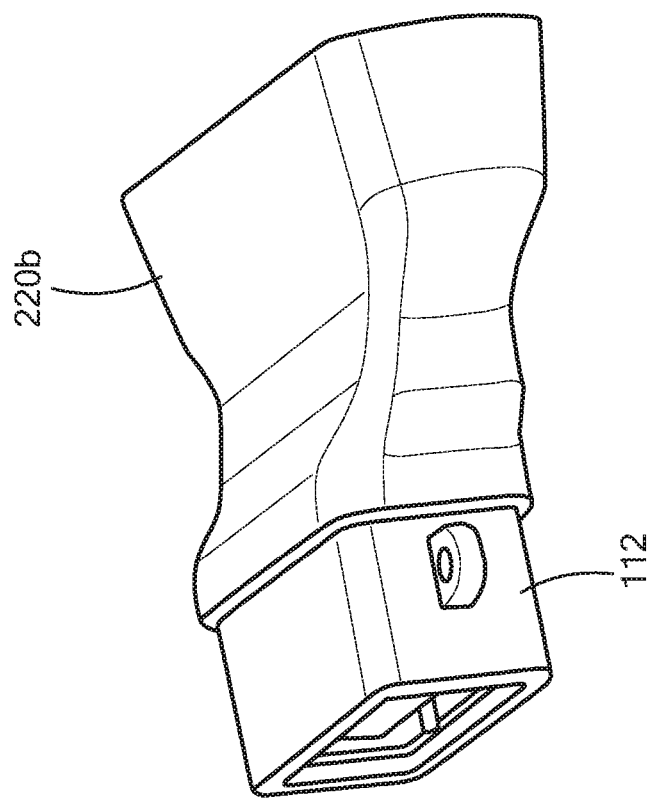
FIG. 7 is an angled view of the two shield components of FIG. 6.
Figure 7:
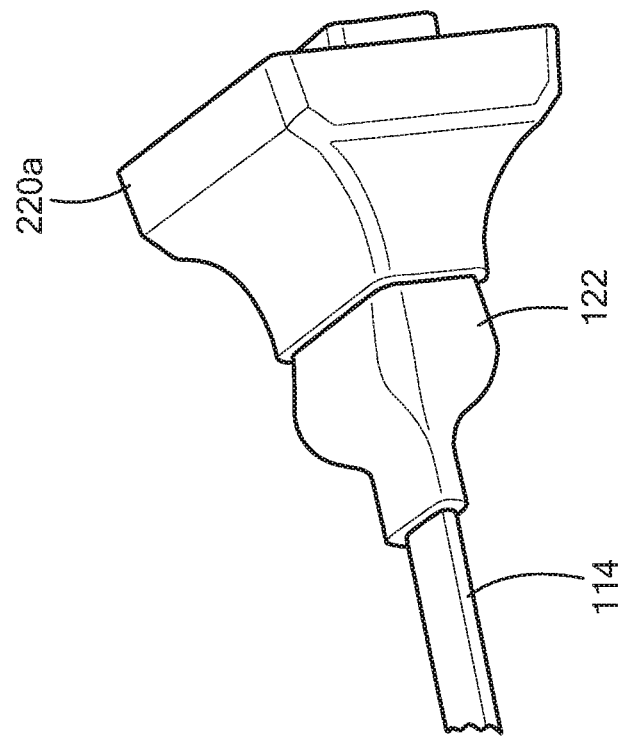

Referring to FIGS. 6 and 7, an ECG lead set configuration 200 includes the ECG lead set 114, the adapter 112 and shield components 220a, 220b. A first electrical connection is formed between the ECG lead set connector 122 and the adapter 112 and a second electrical connection is formed between the adapter 112 and the ECG monitor as described herein with respect to FIGS. 1 to 5.

The shield 220a, 200b are funnel-shaped. The shields 220a, 220b are made of flexible material such as silicone, for example. The shield 220a has a snug fit with the connector 122 and the shield 220b has a snug fit with the adapter 112. For example, the shield 220a is slid on to the connector 122 and the shield 220b is slid on to the adapter 112.

The funnel 130a is configured to allow the first interface 132a of the adapter 112 to pass through to connect with the connector 122. The funnel 130b is configured to allow a connector (not shown) from the ECG monitor to pass through to connect with the second interface 132a. With this arrangement the first and second electrical connections are shielded, for example, from physical objects such as dirt, debris, fluids and so forth.

Elements of different embodiments described herein may be combined to form other embodiments not specifically set forth above. Various elements, which are described in the context of a single embodiment, may also be provided separately or in any suitable subcombination. Other embodiments not specifically described herein are also within the scope of the following claims.

What is claimed is:

1. A physical shielding system comprising:
a shield to protect a first ECG electrical connection and a second ECG electrical connection from objects,
wherein the first ECG electrical connection is formed between a connector of an ECG lead set and an adapter,
wherein the second ECG electrical connection is formed between the adapter and an ECG monitor; and
wherein the shield is configured to securely fit to the adapter without being securely fit to either the ECG lead set or the monitor.

2. The system of claim 1, wherein the shield comprises:
a first funnel-shaped end to shield the first ECG electrical connection from objects; and
a second funnel-shaped end to shield the second ECG electrical connection from objects.

3. The system of claim 1, wherein the shield comprises silicone.

4. An ECG adapter system comprising:
an ECG adapter comprising:
a first interface configured to directly couple with a connector of an ECG lead set to form a first ECG electrical connection;
a second interface configured to directly couple with an ECG monitor to form a second ECG electrical connection; and
a shield securely fit to the adapter, without being securely fit to either the ECG lead set or the ECG monitor, to shield the first ECG electrical connection and the second ECG electrical connection from objects.

5. The system of claim 4, wherein the shield comprises:
a first funnel-shaped end to shield the first ECG electrical connection from objects; and
a second funnel-shaped end to shield the second ECG electrical connection from objects.

6. The system of claim 4, wherein the shield comprises silicone.

* * * * *